United States Patent [19]

Correia

[11] 4,148,832

[45] Apr. 10, 1979

[54] CONTINUOUS PROCESS FOR THE CHLORINATION OF 1,1,1,-TRICHLOROETHANE OR MIXTURES THEREOF

[75] Inventor: Yves Correia, Saint-Auban, France

[73] Assignee: Produits Chimiques Pechiney-Saint-Gobain, France

[21] Appl. No.: 318,991

[22] Filed: Dec. 27, 1972

Related U.S. Application Data

[63] Continuation of Ser. No. 887,769, Dec. 23, 1969, abandoned.

[51] Int. Cl.$^2$ ............................................. C07C 17/00
[52] U.S. Cl. ................................................ 260/658 R
[58] Field of Search ............................ 260/658 R, 660

[56] References Cited

U.S. PATENT DOCUMENTS

| | | | |
|---|---|---|---|
| 2,593,451 | 4/1952 | Hill et al. | 260/654 D |
| 3,344,197 | 9/1967 | Reiche et al. | 260/658 R |
| 3,475,504 | 10/1969 | Kircher et al. | 260/658 R |
| 3,637,875 | 1/1972 | Correia et al. | 260/658 R |

FOREIGN PATENT DOCUMENTS 1097055  12/1967  United Kingdom ................ 260/658 R

*Primary Examiner*—Delbert E. Gantz
*Assistant Examiner*—Joseph A. Boska

[57] ABSTRACT

A continuous process for chlorination of 1,1,1-trichloroethane alone or in admixture with other aliphatic chlorinated $C_1$ to $C_4$ hydrocarbons in a liquid phase reaction with molecular chlorine in the presence of a catalyst selected from the group consisting of ferric chloride, iron oxychloride and mixtures thereof in the absence of light radiations wherein the reaction may be carried out in a single reaction zone at a temperature within the range of 35°–120° C. or in a series of reaction zones in which the effluent from the first reaction zone is introduced into the second reaction zone along with additional chlorine and unsaturated chlorinated hydrocarbon with the temperature in the second reaction zone being less by at least 5° than the temperature in the initial reaction zone.

29 Claims, No Drawings

CONTINUOUS PROCESS FOR THE CHLORINATION OF 1,1,1,-TRICHLOROETHANE OR MIXTURES THEREOF

This is a continuation of application Ser. No. 887,769, filed Dec. 23, 1969, now abandoned.

This invention relates to a continuous process for the liquid phase chlorination of 1,1,1-trichloroethane or of mixtures of chlorinated aliphatic hydrocarbons with 1,1,1-trichloroethane in the presence of a chemical catalyst.

It is known to carry out the photochemical chlorination of 1,1,1-trichloroethane to yield a mixture of symmetrical and unsymmetrical tetrachloroethanes as well as pentachloroethane. However, it is difficult to adapt this photochemical technique to commercial practice, particularly when the 1,1,1-trichloroethane to be chlorinated is in admixture with other chlorinated derivatives of saturated and/or unsaturated hydrocarbons.

It is an object of this invention to provide a continuous process for the chlorination of 1,1,1-trichloroethane alone and more particularly in admixture with other saturated and/or unsaturated chlorinated hydrocarbons in the presence of a chemical catalyst, to obtain chlorinated derivatives of saturated hydrocarbons, and in which the process is capable of being reduced to commercial, large scale operation.

In accordance with the continuous process of this invention, molecular chlorine is reacted with 1,1,1-trichloroethane in the liquid phase, alone or in admixture with other $C_1$ to $C_4$ and preferably $C_2$ aliphatic chlorinated hydrocarbons.

The reaction is carried out in at least one reaction zone at a temperature within the range of 35°-120° C., in the absence of light radiations, but in the presence of a catalyst selected from the group consisting of ferric chloride and iron oxychloride.

In the instance where the catalyst is prepared in situ within the reaction medium, as by reaction of molecular chlorine or iron and/or its oxides, the presence of a low moisture content is desired, such as within the range of 0.005 to 0.1% by weight based on the reaction medium. Generally speaking, the initial reagents will be very slightly moist.

In accordance with an embodiment of this process, molecular chlorine and 1,1,1-trichloroethane in the liquid phase, alone or in admixture with at least one other chlorinated saturated $C_2$ hydrocarbon which does not practically undergo dehydrochlorination under the reaction conditions, such as 1,2-dichloroethane, are passed in a single reaction zone filled with iron turnings and/or its oxides.

In the event that the 1,1,1-trichloroethane to be chlorinated is in admixture with other chlorinated derivatives which may also react with molecular chlorine, it has been observed that chlorination and dehydrochlorination reactions occur simultaneously within the reaction medium, thus releasing a noticeable amount of gaseous hydrochloric acid which tends to entrain a part of the chlorine dissolved in the reaction medium. The chlorine which is swept along by the hydrochloric acid gas is very difficult to recover. Thus the release of hydrochloric acid limits the amount of dissolved chlorine, thus reducing the kinetics of the chlorination reaction of certain sparingly reactive chlorinated olefins, such as trichloroethylene.

In this connection, it has been found that in order to avoid chlorine losses by entrainment of the dissolved chlorine with gaseous hydrochloric acid, it is desirable to carry out the chlorination in two separate reaction zones arranged in series. In the first reaction zone a dehydrochlorination reaction of almost all of the chlorinated derivatives capable of undergoing dehydrochlorination is achieved, such as 1,1,1-trichloroethane and ethyl chloride. This results in a release of hydrochloric acid gas while molecular chlorine is introduced in amounts to provide a dissolved chlorine content in the reaction medium of the first reaction zone within the range of 0.5 to 4 grams per liter of reaction medium. The temperature of the first reaction zone is maintained above 40° C. and preferably within the range of 60°-100° C.

The average residence time of the reactants in the first reaction zone is in the order of 2 to 15 hours and preferably within the range of 2.5 to 5 hours. The average residence time is defined in the present specification as the ratio between the volume of the reaction zone and the volume per hour of effluent from the reaction zone.

The effluent from the first reaction zone is introduced directly into a second reaction zone without pre-treatment. In accordance with the practice of this invention, the second reaction zone receives molecular chlorine at a feed rate to provide a reaction medium containing 2 to 15 grams per liter of dissolved chlorine and preferably an amount within the range of 3 to 9 grams per liter of the reaction medium. It is advantageous to operate the second reaction zone with a dissolved chlorine content that is higher than that in the first zone.

The temperature of the second reaction zone is preferably lower than that of the first zone by at least 5° C. For example, a temperature may be used in the second reaction zone in the range of 35° to about 60° C. and preferably within the range of 47° to 53° C.

The average residence time of the reactants in the second zone is within the range of 1 to 8 hours and preferably 2 to 4.5 hours.

In accordance with an alternate embodiment of the process of this invention, chlorinated aliphatic unsaturated $C_2$ hydrocarbons, such as cis- and trans-dichloroethylene and trichloroethylene can be added to the reaction medium at the stage of the second reaction zone.

In accordance with a further embodiment of this invention, 1,1,1-trichloroethane alone or in admixture with at least one other saturated aliphatic $C_1$ to $C_4$ and preferably $C_2$ chlorinated hydrocarbon, can be introduced into the first reaction zone whereas, in the second reaction zone, besides introducing molecular chlorine and the effluent from the first reaction zone, there can also be introduced at least one unsaturated aliphatic chlorinated $C_2$ hydrocarbon if desired.

In accordance with a practical embodiment of the process which makes use of two reaction zones, molecular chlorine and 1,1,1-trichloroethane which is in a liquid phase in admixture with other aliphatic chlorinated $C_1$ to $C_4$ and preferably $C_2$ hydrocarbons, are passed into the first reaction zone filled with iron turnings and/or iron oxides whereas the effluent from the first reaction zone is passed directly into the second reaction zone which does not contain a filling of iron and/or its oxides.

As described, the process of this invention is particularly suitable for use in the chlorination of 1,1,1-trichloroethane in liquid phase in admixture chiefly with other chlorinated derivatives of aliphatic hydrocarbons. The following are given by way of illustration, but not by way of limitation, of such other chlorinated derivatives, namely: ethyl chloride (0 to 10 molar % and preferably from 2 to 5%), symmetrical dichloroethane (0 to 70 molar %, and preferably from 40 to 60%), unsymmetrical dichloroethane (0 to 20 molar % and preferably from 2 to 10%), 1,1,2-trichloroethane (0 to 70 molar % and preferably from 1 to 20%), symmetrical tetrachloroethane (0 to 70 molar % and preferably from 1 to 10%), unsymmetrical tetrachloroethane (0 to 70 molar % and preferably from 1 to 10%), pentachloroethane (0 to 70 molar % and preferably less than 10%, carbon tetrachloride (0 to 5 molar %), perchloroethylene (less than 1 molar %), trichloroethylene (0 to 20 molar % and preferably from 5 to 7%), cis- and transdichloroethylenes (0 to 70 molar % and preferably 3 to 15% for the -cis form and less than 5% for the -trans form), vinylidene chloride (0 to 70 molar % and preferably less than 5%) and finally vinyl chloride (0 to 70 molar % and preferably less than 25%).

Under the operating conditions of the present process, certain of these chlorinated derivatives, more particularly the $C_2$ unsaturated derivatives, will have their double bond saturated by the action of molecular chlorine. Thus vinyl chloride will be converted to 1,1,2-trichloroethane; trichloroethylene will be converted to pentachloroethane; cis- and trans-dichloroethylenes and vinylidene chloride respectively yield symmetrical and unsymmetrical tetrachloroethanes as described in application Ser. No. 786,735, filed Dec. 24, 1968 in the name of the applicant.

In contrast, carbon tetrachloride, 1,1,2-trichloroethane, symmetrical tetrachloroethane, symmetrical dichloroethane and pentachloroethane practically do not react. The chlorinated derivatives which practically do not react can be used in the chlorination reaction as diluents or as solvents for 1,1,1-trichloroethane or the mixture containing 1,1,1-trichloroethane. In addition to the chlorinated derivatives, the mixture can contain a small proportion (less than 1 molar %) of ethylene, ethane, methane, propane, propylene, and/or butadiene. Under the chlorination reaction conditions of the invention, ethylene yields 1,2-dichloroethane, propylene yields dichloropropanes and butadiene yields 1,2,3,4-tetrachlorobutane.

The molecular chlorine can be used either in the form of liquid chlorine, which is gasified prior to reaction, or in the form of crude chlorine gas, such as is collected at the exit of commercial processes for producing chlorine by electrolysis of aqueous solutions of sodium chloride. Thus it is practically equivalent to use a 99.9% pure liquid chlorine or a 95% purity chlorine, the main impurities being composed of $N_2$, $CO_2$, $O_2$, $H_2$ and CO. The chlorine used can be diluted with gases which are inert under the reaction conditions, such for example as $N_2$, $CO_2$, $O_2$, $H_2$ and CO. The chlorine dilution by inert gases in a molecular ratio up to 1:1 is not detrimental to the reaction but it is undesirable to handle large volumes of inert gases since the productivity of the process is thereby decreased.

The effluent of the chlorination reaction of this invention generally contains different chlorinated derivatives of saturated aliphatic hydrocarbons, iron and molecular chlorine which are dissolved therein. The dissolved chlorine can be eliminated from the effluent either by heating to a temperature of 120° C. and preferably between 40° to 60° C. and/or by entrainment by means of a gas which is inert to the effluent such as nitrogen or air, or by conversion into 1,2-dichloroethane by passing an adequate amount of gaseous ethylene into contact therewith. Furthermore, the iron, in a dissolved state in the effluent, can be eliminated by water extraction. The organic phase which is separated is dried and then distilled or else azeotropically dried, thus allowing the isolation of each of the chlorinated saturated aliphatic hydrocarbon derivatives contained in the effluent.

The chlorination process of this invention can be operated without the necessity of special installations for recovering and/or reducing the total chlorine losses, thus avoiding supplementary steps. These losses are generally below 4 molar % and preferably are reduced to less than 3 molar % of the entire amount of chlorine that is used.

The following examples are given by way of illustration of the practice of this invention, and not by way of limitation:

EXAMPLE 1

100 moles/hour of 1,1,1-trichloroethane, containing about 0.01% by weight water based on the reaction medium, are introduced continuously at 65° C. into a reaction zone composed of an ordinary steel reactor filled with iron turnings. An electrolysis crude chlorine current containing about 3 molar % of inert gases ($CO_2$, $N_2$, $H_2$, $O_2$ and CO) are passed continuously in the reaction zone at a rate that the dissolved chlorine content in the reaction medium is within the range of 1 to 3 grams per liter of reaction medium. The average residence time of the reactants in the reactor is of about 12 hours. The loss of chlorine entrained in the condenser with the inert gases and the hydrochloric acid formed is of 3.8 molar % of the introduced chlorine.

The effluent from the reactor has the following centesimal molar composition:

| | |
|---|---|
| 1,1,1,2-tetrachloroethane | 74 |
| pentachloroethane | 26 |

The effluent contains moreover about 0.035% by weight of ferric chloride, expressed in the form of dissolved iron, derived from the transformation of iron turnings and chlorine in the presence of the very small amount of water indicated hereinabove. The chlorine dissolved in the effluent is almost quantitatively transformed into 1,2-dichloroethane, by passing a current of ethylene. The dissolved iron is separated by water extraction and the organic phase is dried and azeotropically separated by distillation.

EXAMPLE 2

There are introduced continuously, at 70° C., in a first reaction zone in the form of an ordinary steel reactor filled with iron turnings, 100 moles/hour of a mixture composed of: 15 molar % of 1,1,1-trichloroethane, 70 molar % of 1,2-dichloroethane and 15 molar % of trichloroethylene containing about 0.015% by weight of water based on the reaction medium. An electrolysis crude chlorine gas is passed continuously into said reactor at a rate so that the chlorine content dissolved in said mixture is between 1 and 3 grams per liter of reaction medium. The average residence time of the reactants in this reactor is of about 4 hours. The loss of chlorine, entrained in the condenser with the inert gases of said crude chlorine ($CO_2$, $N_2$, $H_2$, $O_2$ and CO) and with the hydrochloric acid, amounts to about 3 molar % of the crude chlorine used. The effluent reactor liquid containing about 0.04% by weight of ferric chloride, expressed in the form of dissolved iron, is introduced into a second reaction zone in the form of an ordinary steel reactor containing no iron turnings. An electrolysis crude chlorine flow is passed into this second reactor at a rate to obtain a dissolved chlorine content of about 6 grams per liter. The reaction medium temperature is of 50° C. and the residence time of the reactants is about 4 hours. The chlorine losses entrained with the inert gases of said crude chlorine and the hydrochloric acid represent 2.5 molar % of the chlorine introduced into the second reactor. The total chlorine losses based on the amount of the chlorine involved into both reactors represent 2.25 molar %. The dissolved chlorine, which has not reacted, is recovered by stripping the second reactor effluent.

The iron content of the liquid effluent of this reactor is substantially the same as that of the liquid effluent of the first reactor.

The following table summarizes the results obtained.

|  | Molar composition of the initial mixture | Molar composition of the effluent of the first reactor | Molar composition of the effluent of the second reactor |
|---|---|---|---|
| 1,1,1-trichloroethane | 15 | 0.75 | 0 |
| 1,2-dichloroethane | 70 | 70.0 | 70 |
| trichloroethylene | 15 | 15.0 | ≈0 |
| 1,1,1,2-tetrachloroethane |  | 11.4 | 12 |
| pentachloroethane |  | 2.85 | 18 |

The iron dissolved in the effluent is removed by washing the effluent with water. The various chlorinated ethane constituents of the organic phase are dried and separated by azeotropical distillation.

EXAMPLE 3

Into a first reaction zone, in the form of an ordinary steel reactor filled with iron turnings, there are introduced continuously at 70°–75° C. 100 moles/hour of a mixture having the following centesimal composition:

|  | moles/hour |
|---|---|
| 1,1,1-trichloroethane | 7 |
| 1,2-dichloroethane | 60 |
| 1,1,2-trichloroethane | 15 |
| 1,1-dichloroethylene | 5 |
| cis- and trans-1,2-dichloroethylene | 7 |
| trichloroethylene | in 6 |

This mixture contains 0.01% by weight of water. An electrolysis crude chlorine flow is passed continuously into said reactor at a rate that the chlorine content dissolved in said mixture is of about 1 gram per liter. The average residence time of the reactants in this reactor is of about 4 hours. The loss of chlorine carried within the condenser with the inert gases of the crude chlorine ($CO_2$, $N_2$, $H_2$, $O_2$ and CO) and with the hydrochloric acid, amounts to about 2.5 molar % of the crude chlorine introduced. The first reactor liquid effluent, containing about 0.035% by weight of ferric chloride, expressed in the form of dissolved iron, is introduced into a second reaction zone composed also of an ordinary steel reactor, but not containing iron turnings. An electrolysis crude chlorine flow is simultaneously passed continuously into this second reactor at a rate to maintain a dissolved chlorine content of between 4 and 6 grams per liter. The reaction medium temperature is 50° C. and the average residence time of the reactants is about 4 hours. The chlorine losses entrained with the inert gases of said crude chlorine and with the hydrochloric acid represent 3 molar % of the chlorine introduced into the second reactor. The liquid effluent iron content of this reactor is substantially the same as that of the first reactor effluent. The total chlorine losses based on the total amount of chlorine introduced into both reactors represent 2.6 molar %. The following table summarizes the results observed.

|  | Molar composition of the initial mixture | Molar composition of the effluent of the first reactor | Molar composition of the effluent of the second reactor |
|---|---|---|---|
| 1,1,1-trichloroethane | 7 | 0.25 | 0 |
| 1,2-dichloroethane | 60 | 60.0 | 60.0 |
| 1,1,2-trichloroethane | 15 | 15.0 | 15.0 |
| 1,1-dichloroethylene | 5 | 0 | 0 |
| cis- and trans-1,2-dichloroethylene | 7 | 0.7 | 0 |
| trichloroethylene | 6 | 6.0 | 0 |
| 1,1,1,2-tetrachloroethane |  | 9.4 | 9.6 |
| 1,1,2,2-tetrachloroethane |  | 6.3 | 7.0 |
| pentachloroethane |  | 2.35 | 8.4 |

The second reactor effluent is treated by a current of ethylene in order to recover the molecular chlorine dissolved therein (4 to 6 g/l) in the form of 1,2-dichloroethane. Then separation of the dissolved iron removal of water and isolation of the chlorinated ethane constituents, as in Example 2, are carried out.

EXAMPLE 4

The same proceedural steps as in Example 3 are carried out, but with the following characteristics and under the following operational conditions:

1ST REACTOR

Centesimal molar composition of the mixture introduced:

| 1,1,1-trichloroethane | 7 |
|---|---|
| 1,2-dichloroethane | 48 |
| 1,1-dichloroethane | 3 |
| 1,1,2,2-tetrachloroethane | 5 |
| vinyl chloride | 20 |
| 1,1-dichloroethylene | 5 |
| cis- and trans-1,2-dichloroethylene | 7 |
| trichloroethylene | 5 | temperature: 70°–75° C.
water content of this composition: 0.015% by weight
chlorine content dissolved in said composition: from 0.9 to 1.2 g/l
average residence time of reactants: 3.6 hours
chlorine losses: about 2.4 molar % of the introduced chlorine
dissolved iron content of the effluent: 0.033% by weight

2ND REACTOR

Centesimal molar composition at the inlet:

| | |
|---|---|
| 1,1,1-trichloroethane | 0.25 |
| 1,2-dichloroethane | 48.0 |
| 1,1-dichloroethane | 3.0 |
| 1,1,2-trichloroethane | 20.0 |
| 1,1,1-2-tetrochloroethane | 9.4 |
| 1,1,2,2-tetrachloroethane | 10.8 |
| pentachloroethane | 2.35 |
| vinyl chloride | 0 |
| 1,1-dichloroethylene | 0 |
| cis- and trans-1,2-dichloroethylene | 1.2 |
| trichloroethylene | 5.0 | temperature: 50° C.
chlorine content dissolved: from 7 to 10 g/liter
residence time of reactants: 2.5 hours
chlorine losses: about 3 molar % of the chlorine introduced into the second reactor
dissolved iron content of the effluent: 0.032 by weight
Centesimal molar composition at the exit:

| | |
|---|---|
| 1,1,1-trichloroethane | 0 |
| 1,2-dichloroethane | 48.0 |
| 1,1-dichloroethane | 2.7 |
| 1,1,2-trichloroethane | 20.3 |
| 1,1,1,2-tetrachloroethane | 9.6 |
| 1,1,2,2-tetrachloroethane | 12.0 |
| pentachloroethane | 7.4 |
| vinyl chloride | 0 |
| 1,1-dichloroethylene | 0 |
| cis- and trans-1,2-dichloroethylene | 0 |
| trichlorethylene | 0 |

The total chlorine losses based on the chlorine introduced into both reactors are of about 2.5 molar %.

The second reactor effluent is treated as in Example 3 in order to: convert the chlorine, eliminate the iron and the water which are dissolved therein, and isolate the various chlorinated ethane constituents.

By way of comparison, the following tests have been conducted:

1ST COMPARATIVE TEST

A chlorination has been carried out as in Example 4 except that the temperature of the second reactor is 65° C., all other operational conditions remaining unchanged. It is observed that the chlorine content dissolved in the 2nd reactor decreases and falls down to about 1 gram per liter and the conversion rate of the trichloroethylene is only 73 molar %.

Hydrochloric acid is evolved from this reactor at the same time as chlorine, thus giving rise to a chlorine loss of 4 molar % based on the total chlorine introduced into both reactors.

2ND COMPARATIVE TEST

The chlorination of the mixture of Example 4 has been carried out but using only a single reactor with the chlorination temperature being 50° C. In order that the trichloroethylene be entirely converted, as in Example 4, without losing more than 2.5 molar % chlorine in the entrained gases, it has been established that an average residence time of the reactants of about 16 hours is necessary.

3RD COMPARATIVE TEST

The chlorination of the mixture of Example 4 has been carried out, but by using only a single reactor, the chlorination temperature being 70°–75° C. In order that the trichloroethylene be entirely converted, as in Example 4, without losing more than 2.5 molar % chlorine in the entrained gases, it has been observed that an average residence time of the reactants of 20 hours is necessary.

EXAMPLE 7

The operation is carried out according to the method of Example 1, but with the following characteristics and under the following operational conditions:

| | |
|---|---|
| 1,1,1-trichloroethane | 50 |
| 1,2-dichloroethane | 50 | water content of this mixture: 0.01% by weight
temperature: 65° C.
dissolved chlorine content in said mixture: 1 to 3 g/l
average residence time of reactants: 9 hours
chlorine losses: about 3.5 molar %
dissolved iron content of the effluent: 0.024% by weight
Centesimal molar composition of the effluent:

| | |
|---|---|
| 1,1,1-trichloroethane | 0 |
| 1,2-dichloroethane | 50 |
| 1,1,1,2-tetrachloroethane | 40 |
| pentachloroethane | 10 |

EXAMPLE 8

The process is carried out according to the method of Example 3, but under the following operational conditions:

1ST REACTOR

Introduction of 65 moles/h of 1,1,1-trichloroethane taken alone
Water content of 1,1,1-trichloroethane: 0.01% by weight
Temperature: 65° C.
Dissolved chlorine content in 1,1,1-trichloroethane: 1 to 2 g/l
Average residence time of reactants: 10 hours
Chlorine losses: about 3.5 molar % of the introduced chlorine
Dissolved iron content of the effluent: 0.023% by weight
Molar composition of the effluent:

| | |
|---|---|
| 1,1,1-trichloroethane | 1 |
| 1,1,1,2-tetrachloroethane | 51.2 |
| pentachloroethane | 12.8 |

2ND REACTOR molar composition at the inlet:

| | |
|---|---|
| effluent of the 1st reactor added with | |
| cis- and trans-1,2-dichloroethylene | 20 |
| trichloroethylene | 15 | introduction of molar chlorine to maintain a dissolved chlorine content of: 5 to 8 g/liter:37.9 mole
temperature: 50° C.
average residence time of reactants: 3 hours
chlorine losses: about 1 molar % of the introduced chlorine dissolved iron content of the effluent: 0.01 to 0.04% by weight molar composition of the effluent:

| | |
|---|---|
| 1,1,1-trichloroethane | 0 |
| 1,1,1,2-tetrachloroethane | 52 |
| 1,1,2,2-tetrachloroethane | 20 |
| pentachloroethane | 28 |
| cis- and trans-1,2-dichloroethylene | 0 |
| trichloroethylene | 0 |

The second reactor effluent is treated as in Example 3. The total chlorine losses based on the chlorine used in both reactors are of about 2.7 molar %.

It will be understood that changes may be made in the details of formulation and operation without departing from the spirit of the invention, especially as defined in the following claims.

I claim:

1. A continuous process for the chlorination of 1,1,1-trichloroethane comprising reacting molecular chlorine with 1,1,1-trichloroethane in the liquid phase in a first reaction zone in the presence of a catalyst selected from the group consisting of ferric chloride, iron oxychloride and mixtures thereof at a temperature above 35° C. and in the absence of light radiation, passing the effluent from the first reaction zone directly into a second reaction zone and reacting said effluent in the second reaction zone with molecular chlorine, with the amount of chlorine introduced into the first reaction zone being an amount sufficient to maintain chlorine dissolved in the reaction medium in an amount within the range of 0.5 to 4 g/l and the amount of chlorine introduced into the second reaction zone being sufficient to maintain a dissolved chlorine content within the range of 2–15 g/l.

2. A process as claimed in claim 1 in which the temperature in the first reaction zone is above 40° C.

3. A process as claimed in claim 1 in which the temperature in the first reaction zone is maintained within the range of 60°–100° C. and in which the temperature in the second reaction zone is at least 5° below the temperature in the first reaction zone.

4. A process as claimed in claim 1 in which the temperature in the first reaction zone is maintained within the range of 60°–100° C. while the temperature in the second reaction zone is maintained within the range of 35°–60° C.

5. A process as claimed in claim 1 in which the temperature in the second reaction zone is maintained within the range of 47°–53° C.

6. A process as claimed in claim 1 in which the chlorine is introduced into the first reaction zone in an amount to maintain the dissolved chlorine in the reaction medium within the range of 0.5 to 4 grams per liter.

7. A process as claimed in claim 1 in which the reactants are maintained in the first reaction zone for a residence time of 2 to 15 hours and in the second reaction zone for a residence time of 1 to 8 hours.

8. A process as claimed in claim 1 in which the reactants are maintained in the first reaction zone for a residence time of 2 to 5 hours and in the second reaction zone for a residence time within the range of 2 to 4.5 hours.

9. A process as claimed in claim 1 in which a chlorinated aliphatic unsaturated $C_2$ hydrocarbon is added at the second reaction zone stage.

10. A continuous process as claimed in claim 1 wherein the first reaction zone contains a catalyst forming material of iron particles and/or iron oxide and the second reaction zone is free from such catalyst forming material.

11. A continuous process as claimed in claim 1 wherein the first reaction zone includes a chloroethylene.

12. A continuous process as claimed in claim 1 wherein the first reaction zone includes at least one unreactive saturated chlorinated hydrocarbon selected from the group consisting of carbon tetrachloride, 1,1,2-trichloroethane, 1,1,2,2-tetrachloroethane, 1,2-dichloroethane and pentachloroethane.

13. A continuous process as claimed in claim 1 which includes the step of feeding a chloroethylene to the first reaction zone with the 1,1,1-trichloroethane.

14. A continuous process for the chlorination of 1,1,1-trichloroethane comprising reacting molecular chlorine with 1,1,1-trichloroethane in the liquid phase in a reaction zone in the presence of a catalyst selected from the group consisting of ferric chloride, iron oxychloride and mixtures thereof at a temperature above 35° C. and in the absence of light radiation.

15. A continuous process as claimed in claim 14, wherein the reaction temperature in the reaction zone is within the range of 35° to 120° C.

16. A continuous process as claimed in claim 14 wherein the catalyst is present in an amount within the range of 0.0025% to 0.2% expressed as the amount of Fe based upon the weight of the liquid reaction medium.

17. A continuous process as claimed in claim 14 wherein the reaction zone also contains at least one $C_1$ to $C_4$ aliphatic chlorinated hydrocarbon.

18. A continuous process as claimed in claim 14 wherein the reaction zone includes at least one $C_2$ unsaturated chlorinated hydrocarbon selected from the group consisting of vinyl chloride, trichloroethylene and dichloroethylenes.

19. A continuous process as claimed in claim 14 wherein the reaction zone includes at least one unreactive saturated chlorinated hydrocarbon selected from the group consisting of carbon tetrachloride, 1,1,2-trichloroethane, 1,1,2,2-tetrachloroethane, 1,2-dichloroethane and pentachloroethane.

20. A continuous process as claimed in claim 14 wherein the reaction zone contains iron particles and/or iron oxides as a catalyst forming medium.

21. A continuous process as claimed in claim 14 wherein the reaction zone includes at least one $C_2$ unsaturated chlorinated hydrocarbon selected from the group consisting of perchloroethylene and vinylidene chloride.

22. A continuous process as claimed in claim 19 wherein the first reaction zone also includes a compound selected from the group consisting of ethyl chloride, unsymmetrical dichloroethane and unsymmetrical tetrachloroethane.

23. A process as claimed in claim 14 in which the reaction medium contains moisture in an amount within the range of 0.005% to 0.1% and the catalyst is obtained by reaction in situ between molecular chlorine and iron particles or oxides of iron in the presence of said moisture.

24. A continuous process for the chlorination of 1,1,1-trichloroethane, at least one chloroethylene and at least one unreactive saturated chlorinated hydrocarbon selected from the group consisting of carbon tetrachloride, 1,1,2-trichloroethane, 1,1,2,2-tetrachloroethane, 1,2-dichloroethane and pentachloroethane comprising reacting molecular chlorine with said mixture in the liquid phase in a reaction zone in the presence of a catalyst selected from the group consisting of ferric chloride, iron oxychloride and mixtures thereof at a temperature above 35° C. and in the absence of light radiation.

25. A continuous process as claimed in claim 24 wherein the chloroethylenes are selected from the group consisting of vinyl chloride, trichloroethylene and dichloroethylenes.

26. A continuous process as claimed in claim 24 wherein the chloroethylenes are selected from the group consisting of perchloroethylene and vinylidene chloride.

27. A continuous process for the chlorination of a mixture of 1,1,1-trichloroethane, at least one chloroethylene and at least one unreacted saturated chlorinated hydrocarbon selected from the group consisting of carbon tetrachloride, 1,1,2-trichloroethane, 1,1,2,2-tetrachloroethane, 1,2-dichloroethane and pentachloroethane, comprising reacting molecular chlorine with said mixture in a first reaction zone in the presence of a catalyst selected from the group consisting of ferric chloride, iron oxychloride and mixtures thereof at a temperature above 35° C. and in the absence of light radiations, passing the effluent from the first reaction zone directly into a second reaction zone and reacting said effluent in the second reaction zone with molecular chlorine.

28. A continuous process for the chlorination of 1,1,1-trichloroethane comprising reacting molecular chlorine with a mixture of 1,1,1-trichloroethane and at least one unreactive saturated chlorinated hydrocarbon selected from the group consisting of carbon tetrachloride, 1,1,2-trichloroethane, 1,1,2,2-tetrachloroethane, 1,2-dichloroethane and pentachloroethane in the liquid phase in a first reaction zone in the presence of a catalyst selected from the group consisting of ferric chloride, iron oxychloride and mixtures thereof at a temperature above 35° C. and in the absence of light radiations, passing the effluent from the first reaction zone directly into a second reaction zone, feeding at least one chloroethylene to the second reaction zone and reacting said effluent and said chloroethylene in the second reaction zone with molecular chlorine.

29. A continuous process for the chlorination of 1,1,1-trichloroethane comprising reacting molecular chlorine with 1,1,1-trichloroethane in the liquid phase in a reaction zone in the presence of a catalyst selected from the group consisting of ferric chloride, iron oxychloride and mixtures thereof at a temperature within the range of 35°-120° C. and in the absence of light radiation, with the amount of chlorine introduced into the reaction zone being an amount sufficient to maintain a dissolved chlorine content in the reaction medium of 0.5 to 4 g/l and the contact time of the reactants in the reaction zone being within the range of 2-5 hours.

* * * * *